(12) United States Patent
Kielin et al.

(10) Patent No.: US 6,753,293 B1
(45) Date of Patent: Jun. 22, 2004

(54) PROCESS FOR COATING SUBSTRATES WITH CATALYTIC MATERIALS

(75) Inventors: Eric J. Kielin, Alexandria, VA (US); Billy T. Upchurch, Virginia Beach, VA (US); David R. Schryer, Hampton, VA (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 315 days.

(21) Appl. No.: 09/607,211

(22) Filed: Jun. 30, 2000

Related U.S. Application Data

(60) Provisional application No. 60/141,729, filed on Jun. 30, 1999.

(51) Int. Cl.[7] ................................. B01J 21/04
(52) U.S. Cl. ...................... 502/439; 502/300
(58) Field of Search ............... 502/439, 324, 502/325, 326, 334, 336, 338, 339, 527.12, 527.14, 527.15, 527.18, 527.19; 427/453, 456, 229, 255.11, 255.19, 255.21, 255.22, 559, 125, 126.2, 126.5, 126.6; 216/76, 101, 55

(56) References Cited

U.S. PATENT DOCUMENTS

| | | | |
|---|---|---|---|
| 4,053,556 A | | 10/1977 | Acres |
| 4,117,082 A | | 9/1978 | Matsuyama |
| 4,422,961 A | * | 12/1983 | Gray ........................... 502/301 |
| 4,639,432 A | * | 1/1987 | Holt et al. ................... 502/324 |
| 4,808,394 A | | 2/1989 | Kolts et al. |
| 4,818,745 A | | 4/1989 | Kolts |
| 4,855,274 A | * | 8/1989 | Upchurch et al. ........... 502/339 |
| 4,912,082 A | * | 3/1990 | Upchurch et al. ........... 502/218 |
| 4,991,181 A | * | 2/1991 | Upchurch et al. ............. 372/59 |
| 4,994,247 A | | 2/1991 | Tooley et al. |
| 5,017,357 A | * | 5/1991 | Kolts et al. .................. 423/437 |
| 5,051,393 A | | 9/1991 | Harrison et al. |
| 5,112,513 A | * | 5/1992 | Bressel et al. .............. 252/79.1 |
| 5,509,557 A | * | 4/1996 | Jimarez et al. ................ 216/95 |
| 5,585,083 A | * | 12/1996 | Kielin et al. .............. 423/245.3 |
| 5,705,082 A | * | 1/1998 | Hinson ......................... 216/95 |
| 5,851,948 A | | 12/1998 | Chuang et al. |
| 6,132,694 A | * | 10/2000 | Wood et al. .............. 423/245.1 |

* cited by examiner

*Primary Examiner*—Stanley S. Silverman
*Assistant Examiner*—Edward M. Johnson
(74) *Attorney, Agent, or Firm*—Helen M. Galus

(57) ABSTRACT

A process for forming catalysts by coating substrates with two or more catalytic components, which comprises the following sequence of steps. First, the substrate is infused with an adequate amount of solution having a starting material comprising a catalytic component precursor, wherein the thermal decomposition product of the catalytic component precursor is a catalytic component. Second, the excess of the solution is removed from the substrate, thereby leaving a coating of the catalytic component precursor on the surface of the substrate. Third, the coating of the catalytic component precursor is converted to the catalytic component by thermal decomposition. Finally, the coated substance is etched to increase the surface area. The first three steps are then repeated for at least a second catalytic component. This process is ideally suited for application in producing efficient low temperature oxidation catalysts.

51 Claims, 1 Drawing Sheet

PROCESS FOR COATING SUBSTRATES WITH CATALYTIC MATERIALS

CLAIM OF BENEFIT OF PROVISIONAL APPLICATION

Pursuant to 35 U.S.C. §119, the benefit of priority from provisional application No. 60/141,729, with a filing date of Jun. 30, 1999, is claimed for this non-provisional application.

ORIGIN OF THE INVENTION

The invention described herein was jointly made by employees of the United States Government and contract employees during the performance of work under a NASA contract which is subject to the provisions of 35 USC 202 in which the contractor has elected not to retain title.

BACKGROUND OF THE INVENTION

1. Field of the Invention

This invention relates generally to the process of coating substrates with one or more catalytic components to form a catalyst. It relates particularly to the process of layering one or more catalytic components onto a honeycomb monolith to form a carbon monoxide oxidation which combines CO and $O_2$ to form $CO_2$, or alternatively, a volatile organic compound oxidation catalyst which combines the compound and $O_2$ to form $CO_2$ and $H_2O$.

2. Description of the Related Art

The catalytic conversion of carbon monoxide to carbon dioxide in the presence of oxygen is useful to a number of fields. Applications in which CO oxidation catalysts may be successfully employed include the following:(i) catalytic removal of CO in air-purification systems, especially for enclosed spaces; (ii) removal of CO in filter canisters, and the like, for personal breathing apparatuses; (iii) removal of CO from combustion products of cigarettes; (iv) removal of CO from exhaust gases expelled from gasoline- and diesel-powered internal combustion engines; and (v) catalytic conversion of dissociation products in $CO_2$ lasers to maximize laser power and life, and minimize laser weight, size, and engineering complexity. Each of these and other applications require a different embodiment of a CO oxidation catalyst and place a different emphasis on one or another quality. Thus, a catalyst for an air-purification system necessarily must have a high throughput, while a catalyst for an internal combustion engine requires the capacity to operate over a broad temperature range, and cost per unit takes on greater significance in the cigarette application. Improvements in CO oxidation catalysts are continually being sought to increase the versatility, effectiveness, durability, activity, and operating life of the CO oxidation catalyst.

Several patents, e.g., U.S. Pat. Nos. 4,912,082 and 4,991,181 to Upchurch and U.S. Pat. Nos. 4,818,745 and 4,808,394 to Kolts, disclose compositions useful to $CO_2$ laser applications. During the operation of a $CO_2$ laser, $CO_2$ decomposes into CO and $O_2$ in the laser's electrical discharge zone. The concentration of the dissociation products increases throughout the laser's operation, while the concentration of $CO_2$ correspondingly decreases. Both the loss of $CO_2$ and the build-up of $O_2$, which scavenges electrons from the $CO_2$ molecules, significantly reduce the lazing power and degrade the performance of the laser. This problem may be addressed either by continually replacing the dissociation products with fresh $CO_2$ during the laser's operation or by using an ambient temperature CO-oxidation catalyst. The former is expensive and, especially for most airborne and space applications, unworkable because of the weight penalty. Hence, the latter is preferred, but the catalyst must have an extended activity life for most applications.

In U.S. Pat. No. 4,994,247 to Tooley and U.S. Pat. No. 5,017,357 to Kolts, CO-oxidation catalyst compositions are disclosed which are suitable for a number of applications including the minimization of CO in tobacco smoke; removal of CO for personal breathing masks, e.g., those worn by miners; and $CO_2$ laser applications. Matsuyama, in U.S. Pat No. 4,117,082 and Harrison, in U.S. Pat. No. 5,051,393, disclose CO-oxidation catalyst compositions developed for use in minimizing carbon monoxide and/or unburnt hydrocarbons from vehicle exhaust. U.S. Pat No. 4,639,432 to Holt discloses CO-oxidation catalyst compositions directed towards the previously stated problems and also towards air-purification or ventilation systems for the removal of CO from confined spaces, especially where traditional ventilation methods are difficult or unfeasible. Examples include nuclear submarines and areas around welding equipment.

In many applications it is also highly desirable, if not necessary, to remove hydrocarbons and other volatile organic compounds from the air via oxidation to $CO_2$ and $H_2O$ without the aid of filters and with minimal heating of the catalyst. By way of example, there has been a long-standing need for a method to remove volatile organic compounds from indoor air i.e., breathable air in enclosed spaces such as homes, automobiles, airplanes, ships, boats, and industrial plants where there may be high concentrations of said compounds. Other significant long-standing needs include the need to purify compressed air and other oxygen-containing gases, as well as the employment of personal safety masks in the removal of volatile organic compounds from the atmosphere. There has also been a need for such a method in selective chemical sensor and catalytic converters for combustion processes, including internal combustion engines which utilize gasoline, diesel, natural gas, and alcohol fuels.

Considering the range of applications and requirements specific to each, there is an ever present need to develop new, effective oxidation catalyst compositions and/or improved processes for preparing effective oxidation catalyst compositions. Any improvement which increases the versatility, effectiveness, durability, activity, and/or operating life of the catalyst or the process for making such, satisfies this need.

Supported catalysts—specifically, supported carbon monoxide oxidation catalysts—may be prepared by (i) coating a support with "catalytic paint"; (ii) impregnation with precipitation agents in one or multiple steps; (iii) impregnation followed by calcination or firing; and (iv) "anchor coating" where a dense, less penetrable support is first coated with another non-catalytic, more penetrable substance to provide a high surface area receptive to further impregnation by catalytic components.

Coating supports with "catalytic paint" is analogous to the method of pill coating employed by the pharmaceutical industry. Cores of support material are placed in a rotating drum and a "paint" slurry is added to coat the cores. The thickness of the catalyst coating is determined by the amount of "paint" added. A serious disadvantage of this method is that the catalyst material may peel from the support (technically termed "spall") resulting in (i) a catalytically inert support and (ii) spalling powder which will likely travel and gather downstream of the catalyst bed to distort or plug the gas flow.

Impregnation methods generally include suspending the support in a solution of the catalytic material and slowly precipitating the catalytic material onto the support or impregnating the support with the precipitant and then using a technique to force precipitation of the catalytic components immediately on the surface. Three major disadvantages are associated with impregnation methods. First, impregnation via precipitating agents may leave unwanted residues. These residues can decompose to form undesirable gases in levels unacceptable for air purification applications. Second, the catalyst precursor materials used often contain catalyst poisons, e.g. chloride, which limit the activity and effectiveness of the catalyst. Third, impregnation—and "anchor coating" and washcoating—often rely on high temperature firing or calcination to complete the coating process. Exposure to high temperatures will reduce the surface area and lower the activity of the resultant catalyst. In addition, impregnation methods involve extra steps which increases the cost of production.

Catalysts may also be prepared in powder form. Unsupported catalysts suffer from dusting, which is particularly vexing for high throughput applications. In addition, they provide poor dispersion of catalytic materials which both reduces the effectiveness and increases the cost of the catalyst for a given application.

There is an ever present need for new, improved processes for the preparation of effective oxidation catalyst compositions. Improvements in the process which increase the versatility, effectiveness, durability, activity, and/or operating life of the oxidation catalyst satisfy this need. There is a long-standing need for an improved, efficient process of coating substrates with catalytic materials.

SUMMARY OF THE INVENTION

The present invention is a process for forming catalysts by coating substrates with one or more catalytic components and comprises the following sequence of steps. First the substrate is infused with an excess of solution having a starting material comprising a catalytic component precursor, where the thermal decomposition product of the catalytic component precursor is a catalytic component. Second, the excess of the solution is removed from the substrate, thereby leaving a coating of the catalytic component precursor on the surface of the substrate. Third, the coating of the catalytic component precursor is converted to the catalytic component by thermal decomposition. This is achieved by heating the coated substance to approximately 300 degrees Celsius, where the rate of heating is controlled to prevent high temperature calcination of the catalytic component precursor and where any remaining starting material is thermally decomposed, oxidized, and/or volatilized without high temperature calcining, thereby leaving only the catalytic component and no residues on the substrate surface. Finally, the coated substance is etched to increase the surface area. This can be achieved by submerging and refluxing the coated substance in a dilute solution of nitric acid.

The first three steps of the above process are repeated in order to successively layer more than one catalytic component on the substrate. In addition, the first step may be improved by infusing the substrate with an excess of solution by vacuum deaeration, and the second step may be improved by removing the excess of the solution by draining away and/or evaporating off the excess of the solution. If the catalyst is "cured" by heating in an atmosphere of a reducing gas prior to its use, its activity may be substantially improved even further. The potential reducing gases include, but are not limited to, carbon monoxide and hydrogen.

Beneficial results are achieved where the process is used to form a catalyst consisting of a substrate and three catalytic components; wherein the substrate is selected from the group comprising ceramics, glass, metals, and fabrics; wherein the ceramic substrate is selected from the group comprising beads, pellets, and monoliths; wherein the first catalytic component is a metal oxide selected from the group comprising manganese oxide, copper oxide, and tin oxide; wherein the second catalytic component is a metal oxide, where this metal oxide is used as a promoter to increase the activity or catalyzing rate of the catalyst, and is selected from the group comprising the oxides of vanadium, chromium, copper, cobalt, manganese, nickel, or iron; and wherein the third catalytic component is a noble metal selected from the group comprising platinum, palladium, rhodium, iridium, ruthenium, osmium, and gold. Especially beneficial results are achieved where the process is used to form a catalyst consisting of a honeycomb monolith ceramic substrate successively coated with tin oxide, iron oxide, and platinum.

EXAMPLE

Figure 1:
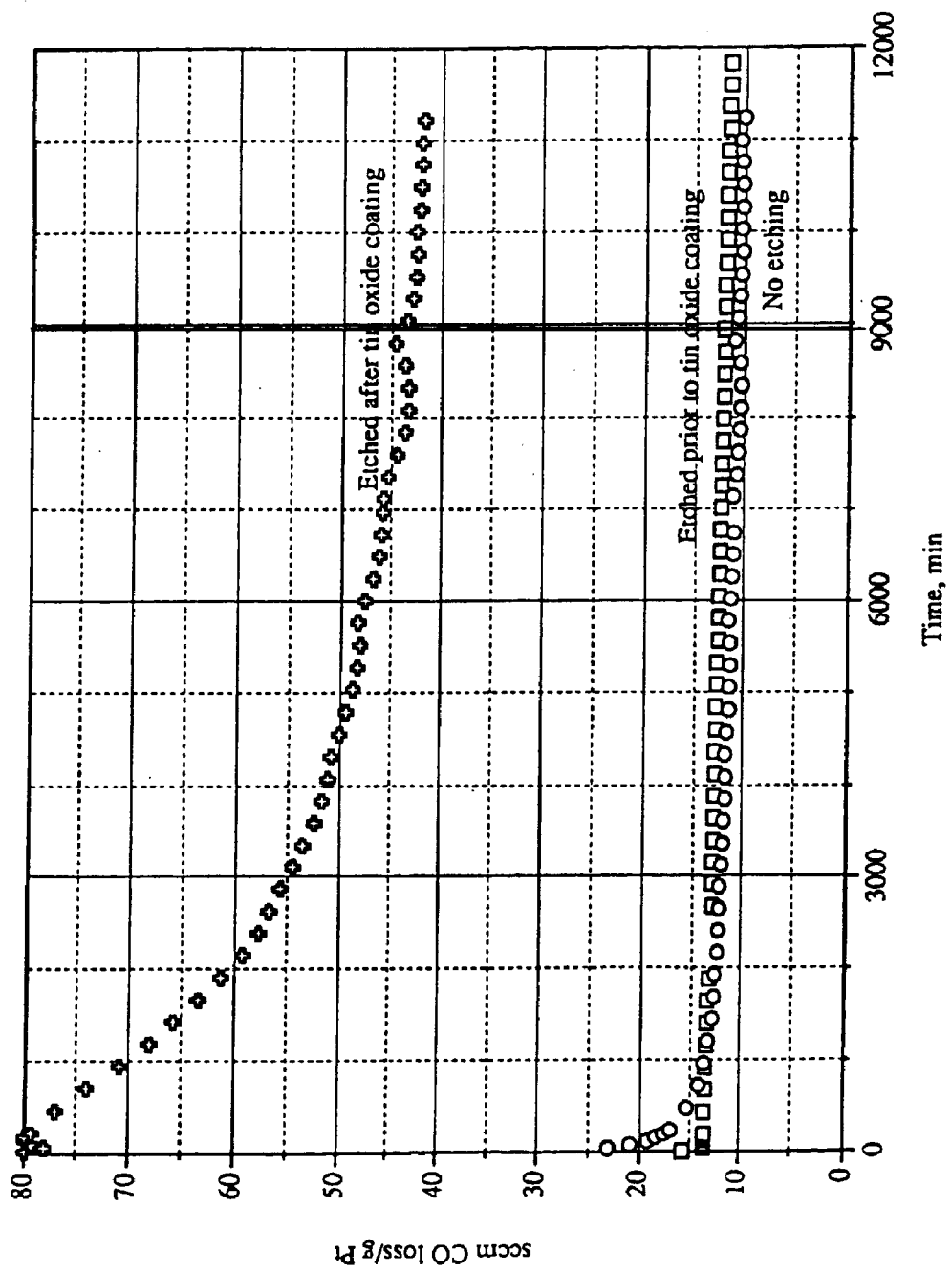
FIG. 1 is a graph representing the effect of $HNO_3$ etching after $SnO_2$ loading on the conversion efficiency of $Pt/SnO_2$ for CO oxidation

SnEH was used to coat all the catalyst samples presented. SnEH is a liquid at room temperature. Acetone can be used to reduce the viscosity and ultimately provide thinner layers or perhaps micro-droplets of SnEH on the surface of the substrate once the acetone has evaporated. Each substrate was vacuum deaerated in SnEH either pure or diluted with acetone. Deaeration facilitates exchange of trapped air in the pores of the monolith with the desired solution insuring a thorough coating with the starting material. After deaearation, the excess solution was shaken, drained or blown from the substrate. Next the SnEH-coated substrate was placed in a muffle furnace and heated from ambient temperature to 200° C. at 1° C./min and held for 3–6 hours and then heated to 300° C. at 1° C./min for 2–6 hours to decompose the SnEH to tin oxide and remove residual organic material, respectively. The above steps were repeated until the desired loading of tin oxide was obtained. The $SnO_2$- coated substrate was etched to increase the surface area of the $SnO_2$ layer which ultimately provides better dispersion of the noble metal. The $SnO_2$ -coated substrates were submerged in 1.5 to 1.6 M nitric acid and heated to near boiling. Etching time varies depending on the desired surface area of the $SnO_2$ -coated substrate. Once etched, the substrates were rinsed with hot DI water to remove any residual nitric acid. Finally the substrates were placed into a muffle furnace and dried at 100° C. for 1 hour then to 250° C. for 2 hours to decompose any nitric acid. CO oxidation activity improved 300–400% for the same amount of noble metal when compared to non-etched substrates or substrates etched prior to the application of the first catalytic component.

The present invention has been described in detail with respect to certain preferred embodiments thereof. However, as is understood by those of skill in the art, variations and modifications in this detail can be made without any departure from the spirit and scope of the present invention as defined in the hereto-appended claims.

What is claimed is:

1. A process of coating the surface of a substrate with catalytic components to form a catalyst, wherein the catalyst is a catalyst matrix having two or more catalytic components which are layered successively on the substrate, comprising the following sequence of steps.
   (a) infusing the substrate with more than an adequate amount of solution having a starting material comprising a catalytic component precursor, wherein the thermal decomposition product of the catalytic component precursor is a catalytic component and wherein an adequate amount of solution is an amount that thoroughly coats the substrate;
   (b) removing from the substrate any solution in excess of an adequate amount, thereby leaving a coating of the catalytic component precursor on the surface of the substrate;
   (c) heating the coated substrate thereby converting the coating of the catalytic component precursor to the catalytic component by thermal decomposition, the catalytic component being a first catalytic component;
   (d) etching the coated substrate;
   (e) repeating steps (a)–(c) for a second catalytic component.

2. The process of claim 1, wherein the sequence of (a), (b), and (c) is repeated in order to successively layer at least a third catalytic component on the substrate.

3. The process of claim 2, wherein the third catalytic component is a metal oxide and this metal oxide is used as a promoter, and wherein the promoter is a catalytic component which increases the activity or catalyzing rate of the catalyst.

4. The process of claim 3, wherein the third catalytic component is a metal oxide selected from the group consisting of the oxides of manganese and iron.

5. The process of claim 4, wherein the third catalytic component is iron oxide.

6. The process of claim 2, wherein the catalyst has three catalytic components.

7. The process of claim 6, wherein the three catalytic components are a first metal oxide, a second metal oxide, and a noble metal.

8. The process of claim 7, wherein the first metal oxide is tin oxide, the second metal oxide is iron oxide, and the noble metal is platinum.

9. The process of claim 2, wherein the sequence of steps (a), (b) and (c) is repeated for one or more of the catalytic components, if required to achieve a desired level of loading.

10. The process of claim 1, wherein the substrate is a substrate selected from the group consisting of ceramics, glass, metals, and fabrics.

11. The process of claim 10, wherein the substrate is a ceramic substrate selected from the group consisting of beads, pellets, and monoliths.

12. The process of claim 11, wherein the ceramic substrate is a monolith.

13. The process of claim 1, wherein the first catalytic component is a metal oxide.

14. The process of claim 13, wherein the first catalytic component is a metal oxide selected from the group consisting of manganese oxide and tin oxide.

15. The process of claim 14, wherein the first catalytic component is tin oxide.

16. The process of claim 1, wherein the second catalytic component is a noble metal.

17. The process of claim 16, wherein the second catalytic component is a noble metal selected from the group consisting of platinum and palladium.

18. The process of claim 17, wherein the second catalytic component is platinum.

19. The process of claim 1, wherein the substrate, now coated with one or more catalytic components, is heated in an atmosphere containing a reducing gas.

20. The process of claim 19, wherein the reducing gas is either carbon monoxide or hydrogen.

21. The process of claim 1, wherein step (a) is modified so that the substrate is infused with an excess of the solution by vacuum deacration.

22. The process of claim 1, wherein stop (b) is modified so that the excess of the solution is removed by draining away and/or evaporating off the excess of the solution.

23. The process of claim 1, wherein step (c) is modified so that the heating of the coated substrate is to approximately 300 degrees Celsius.

24. The process of claim 1, wherein the catalyst formed by said process is used for the oxidation of carbon monoxide.

25. The process of claim 1, wherein the catalyst formed by said process is used for the oxidation of volatile organic compounds.

26. A process for coating the surface of a substrate with catalytic components to form a catalyst, wherein the catalyst comprises at least two catalytic components which are layered successively on the substrate, including the steps of:
   (a) infusing the substrate with more than an adequate amount of solution having a starting material comprising a catalytic component precursor, wherein an adequate amount of solution is an amount that thoroughly coats the substrate;
   (b) removing from the substrate any solution in excess of an adequate amount, thereby leaving a coating of the catalytic component precursor on the surface of the substrate;
   (c) converting the coating of the catalytic component precursor to a first catalytic component;
   (d) etching the coated substrate; and
   (e) repeating steps (a)–(c) to produce a second catalytic component.

27. The process of claim 26, comprising the a step of:
   repeating steps (a), (b), and (c) in order to successively layer at least a third catalytic component on the substrate.

28. The process of claim 27 wherein said step of repeating steps (a), (b), and (c) in order to successively layer at least a third catalytic component on the substrate is performed prior to said step (d) and (e).

29. The process of claim 28, wherein the third catalytic component is a metal oxide and this metal oxide is used as a promoter, and wherein the promoter is a catalytic component which increases the activity or catalyzing rate of the catalyst.

30. The process of claim 29, wherein the third catalytic component is a metal oxide selected from the group consisting of the oxides of manganese and iron.

31. The process of claim 29, wherein the third catalytic component is iron oxide.

32. The process of claim 28, wherein the three catalytic components are a first metal oxide, a second metal oxide, and a noble metal.

33. The process of claim 32, wherein the first metal oxide is tin oxide, the second metal oxide is iron oxide, and the noble metal is platinum.

34. The process of claim 28, wherein at least the steps of (a), (b) and (c) are repeated for one or more of the catalytic components if required to achieve a desired level of loading.

35. The process of claim 26, wherein the substrate is a substrate selected from the group consisting of ceramics, glass, metals, and fabrics.

36. The process of claim 35, wherein the substrate is a ceramic substrate selected from the group consisting of beads, pellets, and monoliths.

37. The process of claim 36, wherein the ceramic substrate is a monolith.

38. The process of claim 26, wherein the first catalytic component is a metal oxide.

39. The process of claim 38, wherein the first catalytic component is a metal oxide selected from the group consisting of manganese oxide and tin oxide.

40. The process of claim 39, wherein the first catalytic component is tin oxide.

41. The process of claim 26, wherein the second catalytic component is a noble metal.

42. The process of claim 41, wherein the second catalytic component is a noble metal selected from the group consisting of platinum and palladium.

43. The process of claim 42, wherein the second catalytic component is platinum.

44. The process of claim 26, wherein the substrate, now coated with one or more catalytic components, is heated in an atmosphere containing a reducing gas.

45. The process of claim 44, wherein the reducing gas is either carbon monoxide or hydrogen.

46. The process of claim 26, wherein step (a) is modified so that the substrate is infused with an excess of the solution by vacuum deaeration.

47. The process of claim 26, wherein step (b) is modified so that the excess of the solution is removed by draining away and/or evaporating off the excess of the solution.

48. The process of claim 26, wherein step (c) is modified so that the heating of the coated substrate is to approximately 300 degrees Celsius.

49. The process of claim 26 wherein said step of converting the coating of the catalytic component precursor to a first catalytic component comprises the step of heating the coated substrate thereby converting the coating of the catalytic component precursor to the catalytic component by thermal decomposition.

50. The process of claim 26, wherein the catalyst formed by said process is used for the oxidation of carbon monoxide.

51. The process of claim 26, wherein the catalyst formed by said process is used for the oxidation of volatile organic compounds.

* * * * *

UNITED STATES PATENT AND TRADEMARK OFFICE
CERTIFICATE OF CORRECTION

PATENT NO. : 6,753,293 B1
DATED : June 22, 2004
INVENTOR(S) : Erik J. Kielin et al.

It is certified that error appears in the above-identified patent and that said Letters Patent is hereby corrected as shown below:

Title page,
Item [75], Inventors, replace "Eric J. Kielin" with -- Erik J. Kielin --.

Signed and Sealed this

First Day of February, 2005

JON W. DUDAS
*Director of the United States Patent and Trademark Office*